(12) United States Patent
Isshiki et al.

(10) Patent No.: US 9,486,946 B2
(45) Date of Patent: Nov. 8, 2016

(54) APPARATUS FOR MANUFACTURING ABSORBENT BODY AND METHOD FOR MANUFACTURING AIR-PERMEABLE MEMBER

(75) Inventors: Hiroshi Isshiki, Kagawa (JP); Osamu Ishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 894 days.

(21) Appl. No.: 13/819,720

(22) PCT Filed: Aug. 22, 2011

(86) PCT No.: PCT/JP2011/068844
§ 371 (c)(1),
(2), (4) Date: May 9, 2013

(87) PCT Pub. No.: WO2012/029574
PCT Pub. Date: Mar. 8, 2012

(65) Prior Publication Data
US 2013/0221558 A1 Aug. 29, 2013

(30) Foreign Application Priority Data
Aug. 31, 2010 (JP) ................................ 2010-194486

(51) Int. Cl.
*B23K 20/00* (2006.01)
*B29C 41/00* (2006.01)
*A61F 13/15* (2006.01)

(52) U.S. Cl.
CPC ......... *B29C 41/00* (2013.01); *A61F 13/15642* (2013.01); *A61F 13/15699* (2013.01); *B23K 20/00* (2013.01)

(58) Field of Classification Search
None
See application file for complete search history.

(56) References Cited

U.S. PATENT DOCUMENTS 1,365,291 A * 1/1921 Gray .................. H01G 4/30
228/212
2,928,932 A * 3/1960 Huggins .............. B23K 9/0035
219/137 R (Continued)

FOREIGN PATENT DOCUMENTS

EP 0 226 939 A2 12/1986
EP 0566427 A2 * 10/1993 ........... A61C 8/0012

(Continued)

OTHER PUBLICATIONS

European Examination Report from corresponding European application No. 11821591.2 dated Sep. 4, 2015 (4 pgs).

(Continued)

*Primary Examiner* — Kiley Stoner
(74) *Attorney, Agent, or Firm* — Brinks Gilson & Lione (57) ABSTRACT

An apparatus for manufacturing an absorbent body of an absorbent article by depositing a liquid absorbent material on an air-permeable member by passing an air that contains the liquid absorbent material in a thickness direction of the air-permeable member, the apparatus including: a plurality of plates that are stacked in the thickness direction, that constitutes the air-permeable member, each of which includes a plurality of air holes that penetrate the plate in the thickness direction and that allow the air to pass, and each of which includes a joining portion for joining to an adjacent plate in the thickness direction in a portion of the plate in which the air holes are not formed, the plurality of air holes of each of the plates being arranged so as to communicate with corresponding air holes of an adjacent plate in the thickness direction, corresponding air holes of all the plates stacked in the thickness direction having a same shape.

4 Claims, 9 Drawing Sheets

(56) References Cited

U.S. PATENT DOCUMENTS

| | | | | | |
|---|---|---|---|---|---|
| 3,187,426 | A | * | 6/1965 | Prohofsky | H05K 3/368 228/139 |
| 3,513,527 | A | * | 5/1970 | Hoy | H02K 15/024 156/222 |
| 3,742,182 | A | * | 6/1973 | Saunders | B23K 26/0661 156/155 |
| 4,245,769 | A | * | 1/1981 | Meginnis | B23K 20/227 228/173.3 |
| 4,296,606 | A | * | 10/1981 | Reider | F23R 3/002 219/101 |
| 4,807,342 | A | * | 2/1989 | Lapeyre | F28F 21/087 165/165 |
| 5,192,623 | A | * | 3/1993 | Gewelber | B23K 1/0014 228/181 |
| 5,530,225 | A | * | 6/1996 | Hajaligol | A24F 47/008 131/194 |
| 5,665,262 | A | * | 9/1997 | Hajaligol | A24F 47/008 131/194 |
| 5,722,826 | A | * | 3/1998 | Tuneberg | A61C 7/16 433/9 |
| 6,359,273 | B1 | * | 3/2002 | Ogawa | B29C 35/12 156/274.4 |
| 2002/0108934 | A1 | * | 8/2002 | Garcia | B23K 26/0846 219/121.67 |
| 2005/0012786 | A1 | * | 1/2005 | Kobayashi | B41J 2/14209 347/68 |
| 2005/0141574 | A1 | * | 6/2005 | Sakano | H01S 5/02423 372/34 |
| 2008/0000892 | A1 | * | 1/2008 | Hirano | B01L 3/50851 219/433 |
| 2008/0296354 | A1 | * | 12/2008 | Crockett | B23K 20/24 228/193 |
| 2008/0301943 | A1 | * | 12/2008 | Liu | B23K 1/0012 29/890.032 |
| 2009/0085984 | A1 | * | 4/2009 | Kojima | B41J 2/14233 347/68 |
| 2009/0244204 | A1 | * | 10/2009 | Ono | B41J 2/14274 347/68 |
| 2010/0075419 | A1 | * | 3/2010 | Inagaki | A61L 27/56 435/402 |
| 2011/0147059 | A1 | * | 6/2011 | Ma | H01L 23/49822 174/258 |
| 2012/0325533 | A1 | * | 12/2012 | Yoshimura | H05K 3/4623 174/258 |
| 2015/0076051 | A1 | * | 3/2015 | Provo | E21B 43/084 210/232 |
| 2015/0115070 | A1 | * | 4/2015 | Wu | B41J 2/14024 239/589 |

FOREIGN PATENT DOCUMENTS

| | | | |
|---|---|---|---|
| EP | 1 943 991 A1 | | 7/2008 |
| JP | H7-119013 | | 5/1995 |
| JP | 11350241 A | * | 12/1999 |
| JP | 2005-235953 A | | 9/2005 |
| JP | 2006-122109 | | 5/2006 |
| JP | 2006123517 A | * | 5/2006 |
| JP | 2007-054219 | | 3/2007 |
| JP | 2007054219 A | * | 3/2007 |
| JP | 2008074034 A | * | 4/2008 |
| JP | 2009-232959 | | 10/2009 |
| JP | 2010087224 A | * | 4/2010 |
| JP | 2010117126 A | * | 5/2010 |
| JP | 2010-178919 | | 8/2010 |
| JP | 2010178919 A | * | 8/2010 |
| WO | WO 2010/090107 A1 | | 8/2010 |

OTHER PUBLICATIONS

Chinese Official Action from corresponding Chinese application No. 201180041759.9 dated May 29, 2014 (6 pgs).
European extended Search Report from corresponding European application No. 11821591.2 dated Jun. 14, 2014 (5 pgs).
Japanese Official Action from corresponding Japanese application No. 2010-194486 dated Jul. 26, 2014 (2 pgs).
European Office Action from corresponding European application No. 11821591.2 dated Feb. 10, 2016 (5 pgs).
International Search Report from corresponding PCT application No. PCT/JP2011/068844 dated Nov. 22, 2011 (4 pgs).
Vietnamese Office Action from corresponding Vietnamese application No. 1-2013-01006 dated Apr. 26, 2016 (3 pgs).
European Communication Pursuant to Article 94(3) EPC from corresponding European application No. 11821591.2 dated Jul. 12, 2016 (3 pgs).

* cited by examiner

B-B CROSS SECTION
FIG. 7B

B-B CROSS SECTION

FIG. 9B

APPARATUS FOR MANUFACTURING ABSORBENT BODY AND METHOD FOR MANUFACTURING AIR-PERMEABLE MEMBER

RELATED APPLICATION

The present application is a 35 U.S.C. §371 national stage filing of International Patent Application No. PCT/JP2011/068844, filed Aug. 22, 2011, to which priority is claimed under 35 U.S.C. §120 and through which priority is claimed under 35 U.S.C. §119 to Japanese Priority Patent Application No. 2010-194486, filed Aug. 31, 2010.

TECHNICAL FIELD

The present invention relates to an apparatus for manufacturing an absorbent body of an absorbent article such as a disposable diaper and a method for manufacturing an air-permeable member that is provided in the manufacturing apparatus in order to shape the absorbent body.

BACKGROUND ART

As examples of an absorbent article that absorbs excreted liquid such as urine or menstrual blood, disposable diapers, sanitary napkins, and the like are used. These absorbent articles include an absorbent body 1 that is produced by forming pulp fibers 2 into a predetermined shape, the pulp fibers 2 serving as an example of liquid absorbent materials.

Figure 1:
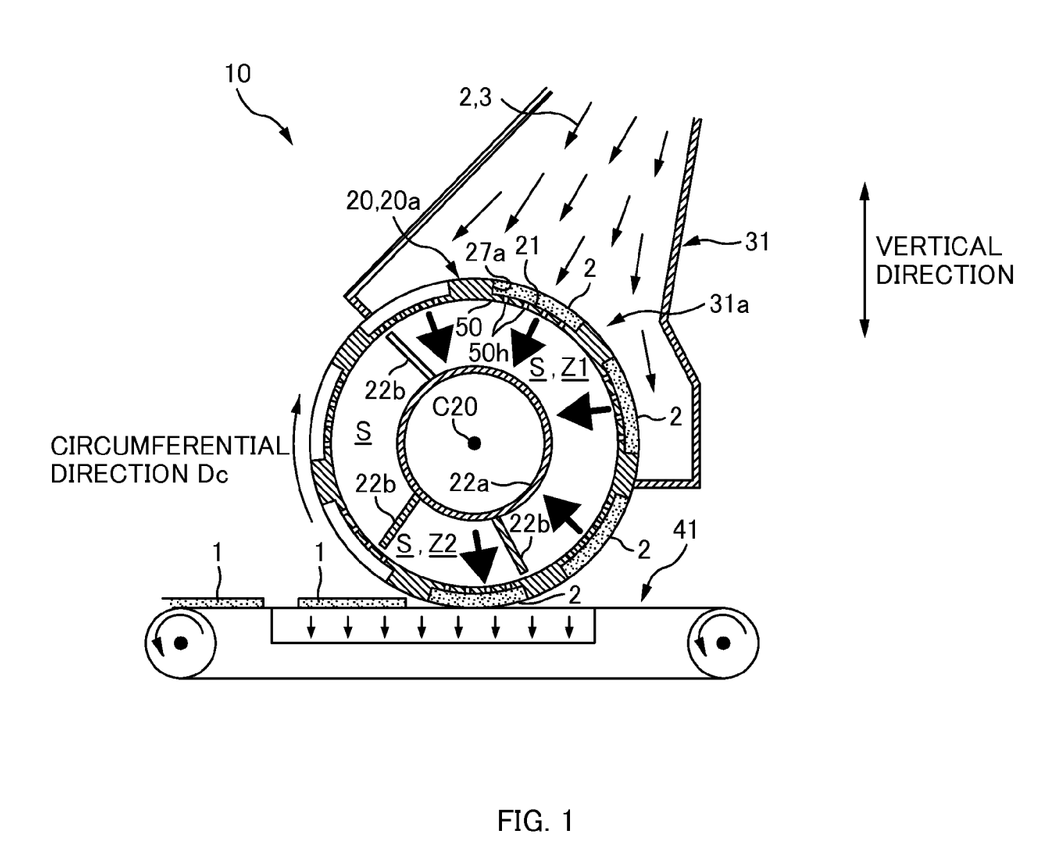
FIG. 1 is a central vertical cross-sectional view of an example of an apparatus 10 for manufacturing an absorbent body 1.

The absorbent body 1 is shaped by a fiber depositing apparatus 10 in a production line (see FIG. 1, for example). The fiber depositing apparatus 10 has a rotating drum 20. While rotating the rotating drum 20 in a circumferential direction Dc, a mixed air 3 in which the pulp fibers 2 are mixed is supplied toward an outer circumferential surface 20a of the rotating drum 20. Thereby, the pulp fibers 2 are deposited in recessed shaping molds 21 on the outer circumferential surface 20a. Thereafter, the deposited pulp fibers 2 are released from the shaping molds 21, and thus absorbent bodies 1 are shaped.

Each shaping mold 21 is formed by, for example, extending an air-permeable member 50 across an opening portion 27a from the inside of the rotating drum 20, the opening portion 27a penetrating the outer circumferential surface 20a of the rotating drum 20. This air-permeable member 50 has as its main body an appropriate plate material, and a plurality of air holes 50h are formed through the plate material in a thickness direction, thereby giving air permeability to the air-permeable member 50.

During the deposition, substantially only the air of the mixed air 3 is sucked from the outside to the inside of the rotating drum 20 through the air-permeable member 50, and the pulp fibers 2 of the mixed air 3 are deposited on the air-permeable member 50. On the other hand, during the release, air is discharged from the inside to the outside of the rotating drum 20 through the air-permeable member 50, and thus the pulp fibers 2 that have accumulated in the shaping mold 21 are removed as an absorbent body 1 (PLT 1).

CITATION LIST

Patent Literature

[PLT 1] JP 2009-232959A

SUMMARY OF INVENTION

Technical Problem

From the point of view of the productivity and the like, there is a demand for more efficient deposition of pulp fibers in the shaping mold 21. That is to say, it is desired to increase the amount of pulp fibers which are deposited in the shaping mold 21 per unit time. A measure to achieve this is to increase the air flow rate through the air-permeable member 50. Specifically, increasing the aperture ratio of the air-permeable member 50 (the ratio of the total area of the air holes 50h to the area of the air-permeable member 50 which faces the opening portion 27a) is conceivable.

Figure 2A:
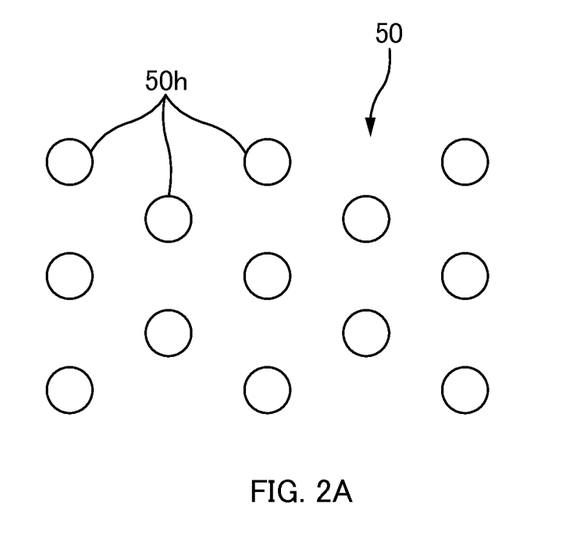
FIG. 2A is a plan view of an air-permeable member 50 in which air holes 50h are arranged at a low density.

It is established, however, that the hole diameter of the air holes 50h is set within a range of, for example, 0.1 mm to 1 mm based on the condition that the passage of the pulp fibers 2 should be restricted, and this hole diameter cannot be easily changed. For this reason, the aforementioned aperture ratio is increased by decreasing the distances between the air holes 50h, from a state shown in FIG. 2A to a state shown in FIG. 2B, and closely arranging the air holes 50h at a high density.

Figure 2B:
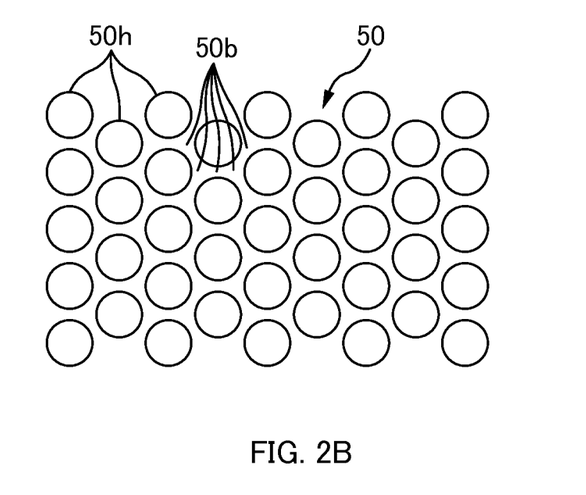
FIG. 2B is a plan view of the air-permeable member 50 in which the air holes 50h are arranged at a high density.

However, as shown in FIG. 2B, reducing the distances between the air holes 50h decreases the strength of portions 50b between the air holes 50h. That is, the portions 50b in which the air holes 50h are not formed becomes weak. Then, due to the repeated suction and discharge of air through the air holes 50h as described above, fatigue failure starting from those portions 50b is likely to occur to the air-permeable member 50. This means that the durability of the air-permeable member 50 would be deteriorated.

On the other hand, as an idea for improving the strength of those portions 50b, increasing the thickness of the air-permeable member 50 is conceivable. However, an etching method is preferable as the method that can closely form the foregoing minute holes having a diameter of 0.1 to 1 mm; in the etching method, the holes 50h would be tapered holes 50t (cone-shaped holes) as shown in the enlarged cross-sectional view of FIG. 3A if a target plate material 50 has a large thickness.

Figure 3A:
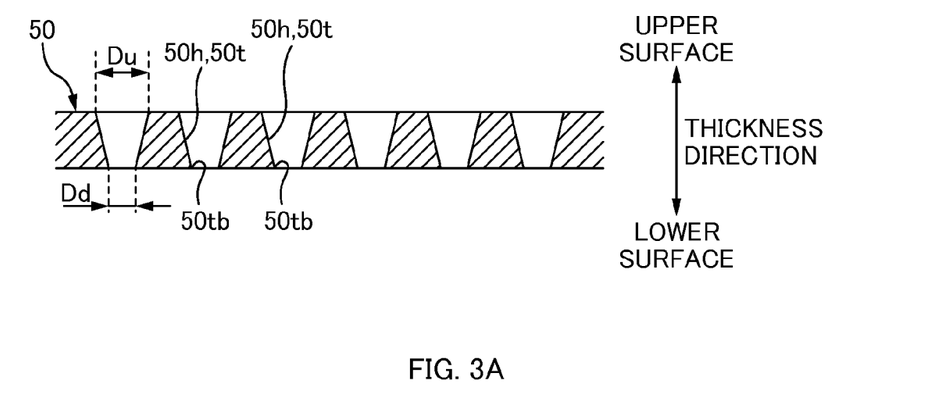
FIG. 3A is an explanatory diagram of tapered holes 50t that are formed in a plate material 50 by an etching method.

Specifically, in the etching method, the upper surface of the plate material 50 is coated with a protective coating having an arrangement pattern of the air holes 50h. Thereafter, portions that are not coated with the protective coating are selectively corroded with an etchant, and holes that penetrate the plate material 50 are formed. At this time, the extent of corrosion differs between the upper surface side and the lower surface side of the plate material 50. Thus, generally, formed are the tapered holes 50t having a larger diameter on the upper surface side and a smaller diameter on the lower surface side, and furthermore. The difference between the hole diameter Du on the upper surface and the hole diameter Dd on the lower surface becomes larger as the plate material 50 becomes thicker.

Figure 3B:
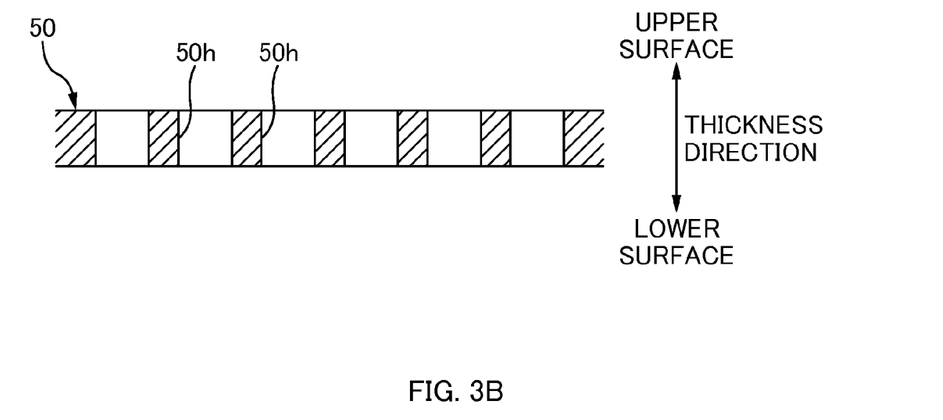
FIG. 3B is an explanatory diagram of a preferred hole shape of the air holes 50h.

There is a problem that narrowed sections 50tb of the foregoing tapered holes 50t on the lower surface side are likely to be clogged during the deposition of pulp fibers. That is to say, from the point of view of preventing the clogging, it is desirable that the air holes 50h have a straight-sided hole shape whose planar shape is the same through the entire length in the thickness direction, as shown in FIG. 3B. However, this is difficult to achieve.

The invention was made in light of conventional problems as described above, and an object thereof is to solve the problem of the decrease in the durability of the air-permeable member and the problem of the clogging of the air-permeable member during deposition of the liquid absorbent material; these problems may arise when seeking an increase in the efficiency of depositing the liquid absorbent material in the air-permeable member.

Solution to Problem

In order to address the above-described problem, a primary aspect of the invention is an apparatus for manufacturing an absorbent body of an absorbent article by depositing a liquid absorbent material on an air-permeable member by passing an air that contains the liquid absorbent material in a thickness direction of the air-permeable member, the apparatus including:
  a plurality of plates
    that are stacked in the thickness direction,
    that constitutes the air-permeable member,
  each of which includes a plurality of air holes that penetrate the plate in the thickness direction and that allow the air to pass, and
  each of which includes a joining portion for joining to an adjacent plate in the thickness direction in a portion of the plate in which the air holes are not formed,
    the plurality of air holes of each of the plates being arranged so as to communicate with corresponding air holes of an adjacent plate in the thickness direction,
    corresponding air holes of all the plates stacked in the thickness direction having a same shape.

Further, a method for manufacturing an air-permeable member,
  the air-permeable member being used when shaping an absorbent body of an absorbent article by depositing a liquid absorbent material,
  the air-permeable member allowing an air that contains the liquid absorbent material to pass in a thickness direction of the air-permeable member,
  the air-permeable member restricting passage of the liquid absorbent material,
  the method including:
    forming a plurality of plates each of which has a plurality of air holes that penetrate the plate in the thickness direction,
    the forming including forming air holes of the plurality of air holes into a same shape, the air holes being ones that exist in all of the plates to be stacked and that should communicate with one another;
    stacking the plurality of plates in the thickness direction while adjusting adjacent air holes in the thickness direction so that the adjacent air holes communicate with one another; and
    joining adjacent plates of all of the stacked plates at a portion in which the air holes are not formed.

Features of the invention other than the above will become clear by reading the description of the present specification with reference to the accompanying drawings.

Advantageous Effects of Invention

According to the invention, it is possible to solve the problem of the decrease in the durability of the air-permeable member and the problem of the clogging of the air-permeable member during deposition of the liquid absorbent material, which may arise when an increase in the efficiency of accumulating the liquid absorbent material using the air-permeable member is sought.

DESCRIPTION OF EMBODIMENTS

At least the following matters will be made clear by reading the description of the present specification with reference to the accompanying drawings.

An apparatus for manufacturing an absorbent body of an absorbent article by depositing a liquid absorbent material on an air-permeable member by passing an air that contains the liquid absorbent material in a thickness direction of the air-permeable member, the apparatus including:
  a plurality of plates
    that are stacked in the thickness direction,
    that constitutes the air-permeable member,
  each of which includes a plurality of air holes that penetrate the plate in the thickness direction and that allow the air to pass, and
  each of which includes a joining portion for joining to an adjacent plate in the thickness direction in a portion of the plate in which the air holes are not formed,
    the plurality of air holes of each of the plates being arranged so as to communicate with corresponding air holes of an adjacent plate in the thickness direction,
    corresponding air holes of all the plates stacked in the thickness direction having a same shape.

With this apparatus for manufacturing an absorbent body, the thickness of each plate can be reduced, and therefore the difference in the hole diameter between the upper surface and the lower surface of the plate can be decreased. That is to say, the air holes of each plate can have a substantially straight-sided hole shape. Moreover, corresponding air holes of all the plates stacked in the thickness direction have the same hole shape. Thus, each air hole of the air-permeable member, which is formed by the air holes of these plates communicating in the thickness direction, has a generally straight-sided hole shape as a whole. This makes it possible to effectively prevent clogging when the liquid absorbent material is being deposited.

Moreover, since the plurality of plates are stacked and integrally joined together, the air-permeable member has enhanced rigidity and is not easily deformed. Thus, the bending deformation of the plates that may repeatedly occur during the deposition of the liquid absorbent material also is reduced as the whole, and therefore the bending stress that acts on the portion in which the air holes are not formed is also reduced. This makes it possible to effectively prevent fatigue failure of that portion.

Furthermore, in each plate, the joining portion is formed in the portion in which the air holes are not formed. This enables a joining area of the joining portion to be as large as possible and can increase the joining strength between plates. Also, this can effectively increase the level of integration between the portion in which the air holes are not formed and a counterpart portion adjacent in the thickness direction. Thus, the strength of those portions themselves is also improved. Consequently, it is possible to prevent effectively breakage of those portions.

From the above, it is possible to solve a problem of the decrease in the durability of the air-permeable member and a problem of the clogging.

In such an apparatus for manufacturing an absorbent body, it is desirable that the plurality of air holes of each of the plates are formed by etching, and the joining portion is formed by diffusion welding.

With this apparatus for manufacturing an absorbent body, the air holes are formed by etching. Therefore, a large number of air holes having a small diameter can be closely arranged at a high density, in which the spacing between the holes is narrow. This can increase the aperture ratio of the air-permeable member, so that the deposition efficiency can improved.

Moreover, the joining portions are formed by diffusion welding. Therefore, those joining portions are formed by joining in surface-to-surface contact a portion of base materials of the respective plates in which the air holes are not formed. Accordingly, it can be said that that portion and a counterpart portion of an adjacent plate in the thickness direction are integrated without an interposer. Consequently, the joining strength between the portions of the respective plates in which the air holes are not formed can be enhanced.

In such an apparatus for manufacturing an absorbent body, it is desirable that each of the plates has a thickness of 0.05 mm to 0.5 mm.

With this apparatus for manufacturing an absorbent body, each plate has a thickness equal to or less than 0.5 mm. Therefore, even if the holes are formed by an etching method, it is possible to reduce the difference between the hole diameter on the upper surface and the hole diameter on the lower surface of each plate. That is to say, the air holes of each plate can have substantially straight-sided hole shapes. Moreover, each plate has a thickness equal to or more than 0.05 mm. This can increase the rigidity of the plates, so that the rigidity of the air-permeable member constituted by these stacked plates can be enhanced.

In such an apparatus for manufacturing an absorbent body, it is desirable that each of the plates has at least two reference holes that are different from the air holes and that penetrate the plate in the thickness direction, and the reference holes are formed so that adjacent reference holes in the thickness direction communicate with one another when corresponding air holes of all of the plates stacked in the thickness direction communicate with one another.

With this apparatus for manufacturing an absorbent body, inserting the bar member into the reference holes of the plurality of plates stacked in the thickness direction is sufficient to align these plates in a state where corresponding air holes communicate with one another. This easily enables the air holes of the stacked plates to communicate with one another.

In such an apparatus for manufacturing an absorbent body, it is desirable that the apparatus further comprises a cylindrical rotating drum that continuously rotates in a circumferential direction, the air-permeable member is provided so as to cover an opening portion disposed in an outer circumferential surface of the rotating drum, an internal space and an external space of the rotating drum are in air-permeably communication through the air-permeable member, a supply duct that supplies the air toward the outer circumferential surface of the rotating drum from outside is provided at a first position in the circumferential direction, a pressure of an internal space of the rotating drum that corresponds to the first position is maintained at a negative pressure that is lower than that of the external space, when the air-permeable member passes the first position, the air in the supply duct is sucked through the air-permeable member into the internal space of the rotating drum and the absorbent body is deposited on the air-permeable member, a release position at which the absorbent body is released from the air-permeable member is set at a position downward from the first position in the circumferential direction, and a pressure of an internal space of the rotating drum that corresponds to the release position is maintained at a pressure equal to ore higher than that of the external space.

With this apparatus for manufacturing an absorbent body, it is possible to effectively achieve the above-described operation and effect. That is to say, when the air-permeable member passes the first position, the air-permeable member is drawn by air, and the drawing force acts radially inwardly in the rotation of the rotating drum. On the other hand, when the air-permeable member passes the release position, the air-permeable member is drawn by air, and the drawing force acts radially outwardly in the rotation of the rotating drum. In this way, the air-permeable member undergoes repeatedly an external force whose direction is inverted, and therefore there is a risk that fatigue failure finally occurs to the air-permeable member. In this respect, the air-permeable member is formed from the plurality of plates that are stacked and integrated by joining, and accordingly has enhanced rigidity. Thus, deformation of the air-permeable member when acted on by the above-described external forces is effectively suppressed, and consequently the fatigue failure is unlikely to occur.

Further,

A method for manufacturing an air-permeable member, the air-permeable member being used when shaping an absorbent body of an absorbent article by depositing a liquid absorbent material, the air-permeable member allowing an air that contains the liquid absorbent material to pass in a thickness direction of the air-permeable member, the air-permeable member restricting passage of the liquid absorbent material, the method including:

forming a plurality of plates each of which has a plurality of air holes that penetrate the plate in the thickness direction, the forming including forming air holes of the plurality of air holes into a same shape, the air holes being ones that exist in all of the plates to be stacked and that should communicate with one another;

stacking the plurality of plates in the thickness direction while adjusting adjacent air holes in the thickness direction so that the adjacent air holes communicate with one another; and joining adjacent plates of all of the stacked plates at a portion in which the air holes are not formed.

With this method for manufacturing an air-permeable member, the thickness of each plate can be reduced, and therefore the difference in the hole diameter between the upper surface and the lower surface of each plate can be decreased. That is to say, the air holes of each plate can have a substantially straight-sided hole shape. Moreover, corresponding air holes of all the plates stacked in the thickness direction have the same hole shape. Thus, each air hole of the air-permeable member, which is formed by the air holes of these plates communicating in the thickness direction, has a generally straight-sided hole shape as a whole. This makes it possible to effectively prevent clogging when the liquid absorbent material is being deposited.

Moreover, since the plurality of plates are stacked and integrally joined together, the air-permeable member has enhanced rigidity and is not easily deformed. Thus, the bending deformation of the plates that may repeatedly occur during deposition of the liquid absorbent material also is reduced as the whole, and therefore the bending stress that acts on the portion in which the air holes are not formed also is reduced. This makes it possible to effectively prevent fatigue failure of the portion.

Furthermore, in each plate, the joining portion is formed in the portion in which the air holes are not formed. This enables a joining area of that joining portion to be as large as possible and can increase the joining strength between the plates. Also, this can effectively increases the level of integration between the portion in which the air holes are not formed and a counterpart portion adjacent in the thickness direction. Thus, the strength of those portions themselves is also improved. Consequently, it is possible to prevent effectively breakage of those portions.

From the above, it is possible to solve the problem of the decrease in the durability of the air-permeable member and the problem of clogging.

In such a method for manufacturing an air-permeable member, it is desirable that the method further comprises forming in each of the plurality of plates at least two reference holes that are different from the air holes and that penetrate the plate in the thickness direction, in the forming of the reference holes, the reference holes are formed so that adjacent reference holes in the thickness direction communicate with one another when corresponding air holes of all of the plates stacked in the thickness direction communicate with one another.

With this method for manufacturing an air-permeable member, inserting the bar member into the reference holes of the plurality of plates stacked in the thickness direction is sufficient to align the plates in a state where corresponding air holes communicate with one another. This easily enables the air holes of the stacked plates to communicate with one another.

In such a method for manufacturing an air-permeable member, it is desirable that in the stacking, a bar member is inserted into adjacent reference holes in the thickness direction so as to penetrate the plurality of plates that have been stacked or so as to penetrate the plurality of plates while stacking the plurality of plates.

With this method for manufacturing an air-permeable member, the bar member is inserted into the reference holes. Therefore, the plates are aligned in a state where corresponding air holes communicate with one another. This easily enables the air holes of the stacked plates to communicate with one another.

In such a method for manufacturing an air-permeable member, it is desirable that in the joining step, in a state where the bar member has been inserted into the reference holes, the adjacent plates are joined by diffusion welding at the portion in which the air holes are not formed.

With this method for manufacturing an air-permeable member, diffusion welding is performed in a state where the bar member has been inserted into the reference holes. This can reliably prevent misalignment of the plates that may occur during the diffusion welding. This makes it possible to reliably manufacture an air-permeable member with air holes having substantially straight-sided shapes.

The Present Embodiment

Overall Configuration of Manufacturing Apparatus 10 for Absorbent Body 1

FIG. 1 is a central vertical cross-sectional view of an apparatus 10 for manufacturing an absorbent body 1.

The apparatus 10 for manufacturing the absorbent body 1 is a so-called fiber depositing apparatus in which pulp fibers 2 serving as a liquid absorbent material are deposited to shape the absorbent body 1.

The main configuration of the apparatus 10 includes: for example, (1) a rotating drum 20 that continuously rotates in a circumferential direction Dc (for example, clockwise) about a horizontal axis C20 serving as the center of rotation; (2) a supply duct 31 that discharges and supplies a mixed air 3 containing the pulp fibers 2 (corresponding to an air) from a supply opening portion 31a to an outer circumferential surface 20a of the rotating drum 20, the supply opening portion 31a being disposed at a predetermined position of the rotating drum 20 (corresponding to a first position); and (3) a suction conveyor 41 that is disposed downward from the supply duct 31 in the circumferential direction Dc and that sucks absorbent bodies 1 to release them from shaping molds 21 on the outer circumferential surface 20a of the rotating drum 20 and conveys the released absorbent bodies 1.

In the following description, the circumferential direction Dc of the rotating drum 20 is simply referred to as the "circumferential direction", and a direction in which the horizontal axis C20 of the rotating drum 20 extends (direction that is perpendicular to the paper surface of FIG. 1) is referred to as a "width direction", a "left-and-right direction", or a "CD direction".

The rotating drum 20 is substantially cylindrical, and, on its outer circumferential surface 20a, there are provided the shaping molds 21 each having a recessed shape corresponding to the shape of the absorbent body 1 to be formed, the shaping molds 21 being provided at a predetermined pitch in the circumferential direction Dc. An air-permeable member 50 is provided in each shaping mold 21 and constitutes a bottom face of it, and an internal space of the shaping mold 21 communicates with an internal space of the rotating drum 20 through the air-permeable member 50 so as to allow the passage of air.

A cylindrical partition wall 22a is provided in the internal space of the rotating drum 20 coaxially with the rotating drum 20, and thus a substantially closed space S having a doughnut shape is formed on an inner circumferential side of the rotating drum 20. Moreover, this substantially closed space S is divided into zones in the circumferential direction Dc by a plurality of partition walls 22b; for example, a first zone Z1 shown in FIG. 1 is maintained in a negative pressure lower than the outside atmospheric pressure, and a second zone Z2 downstream therefrom is maintained at a pressure slightly higher than or equal to the outside atmospheric pressure. The supply opening portion 31a of the above-described supply duct 31 is disposed so as to correspond to the first zone Z1, and the above-described suction conveyor 41 is disposed so as to correspond to the second zone Z2.

Thus, with this fiber depositing apparatus 10, the absorbent body 1 is formed in the following manner. First, when a shaping mold 21 passes through the position of the supply duct 31 due to the rotation of the rotating drum 20, the mixed air 3 is discharged from and supplied by the supply opening portion 31a, and substantially only the air component of the mixed air 3 is drawn in through the air-permeable member 50 on the bottom of that shaping mold 21. Thus, the pulp fibers 2 in the mixed air 3 are deposited onto the air-permeable member 50. Then, when the shaping mold 21 has passed the supply opening portion 31a and reaches a position opposing the suction conveyor 41, the pulp fibers 2 in the shaping mold 21 are sucked outwardly by suction of the suction conveyor 41 and successively released from the shaping mold 21. Subsequently, the pulp fibers 2 are conveyed by the suction conveyor 41 as an absorbent body 1.

Incidentally, it is also possible to provide a polymer injection pipe, which is not shown, within the supply duct 31 and discharge a superabsorbent polymer from an opening of the polymer injection pipe toward the outer circumferential surface 20a. In this case, the superabsorbent polymer also serves as the liquid absorbent material.

Rotating Drum 20

Figure 4:
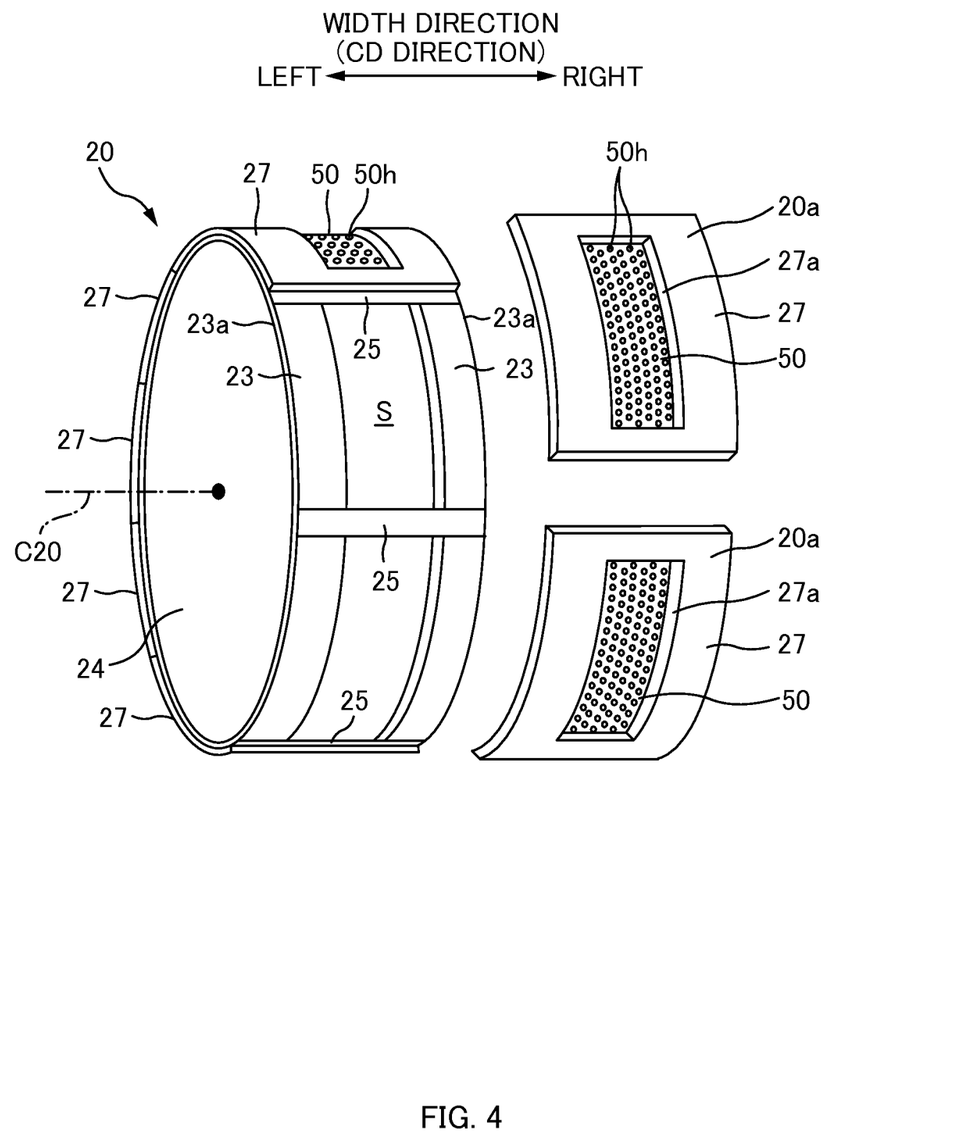
FIG. 4 is an exploded perspective view of a rotating drum 20.

FIG. 4 is an exploded perspective view of the rotating drum 20.

The rotating drum 20 includes: a pair of ring members 23 and 23 that are arranged almost symmetrically relative to a center in the CD direction left between them; a plurality of coupling plates 25, 25, . . . that are provided in the circumferential direction Dc at a predetermined pitch and couple the pair of ring members 23 and 23 to each other; and a plurality of shaping mold plates 27, 27, . . . that extend between two adjacent coupling plates 25 in the circumferential direction Dc and constitute the outer circumferential surface 20a of the rotating drum 20.

The pair of ring members 23 are rings having the same perfect circular shape. Of a pair of the circumferential edges 23a of each ring member 23 in the CD direction, the circumferential edge 23a that faces an outer side in the CD direction is provided with a circular wall 24 having a similar shape to the perfect circular shape of the ring member 23, and thereby the circumferential edge 23a is closed. Thus the aforementioned substantially closed space S is formed on the inner side of the ring members 23.

Each shaping mold plate 27 is an arcuate plate 27 whose length is the same as the circumferential length of the outer circumferential surface 20a of the rotating drum 20 divided equally by the number of shaping molds 21 to be provided (seven, in this example). On the planar center of the arcuate plate 27, an opening portion 27a is formed which has a shape corresponding to the shape into which the absorbent body 1 is to be formed. As shown in the exploded perspective view of the shaping mold plate 27 in FIG. 5, the opening portion 27a is covered with the air-permeable member 50 from the inner side of the rotating drum 20, and this air-permeable member 50 constitutes the bottom face of the shaping mold 21 on which the pulp fibers 2 are to be deposited. The air-permeable member 50 is fixed by means such as welding, continuously or intermittently on the entire edge of the opening portion 27a. In this example, one opening portion 27a that constitutes a shaping mold 21 is formed for each shaping mold plate 27, but the invention is not limited to this. For example, two or more opening portions 27a may also be formed for each shaping mold plate 27.

Figure 6A:
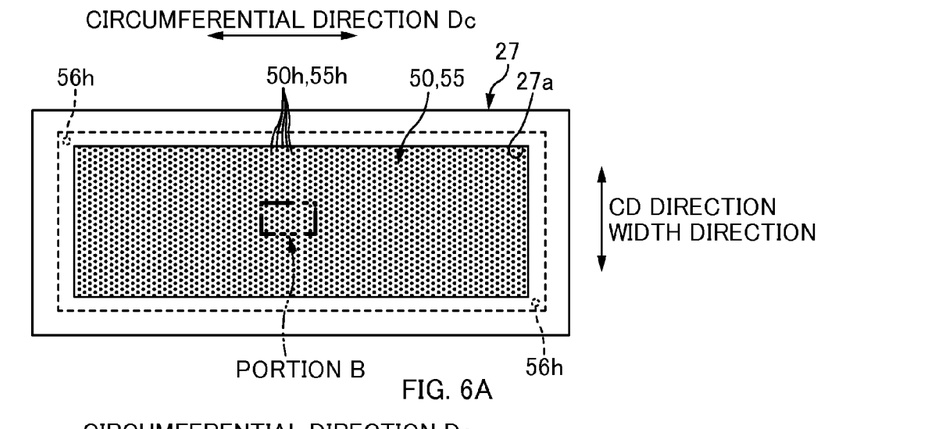
FIG. 6A is a plan view of the air-permeable member 50 in a state in which it is attached to the shaping mold plate 27.
Figure 6B:
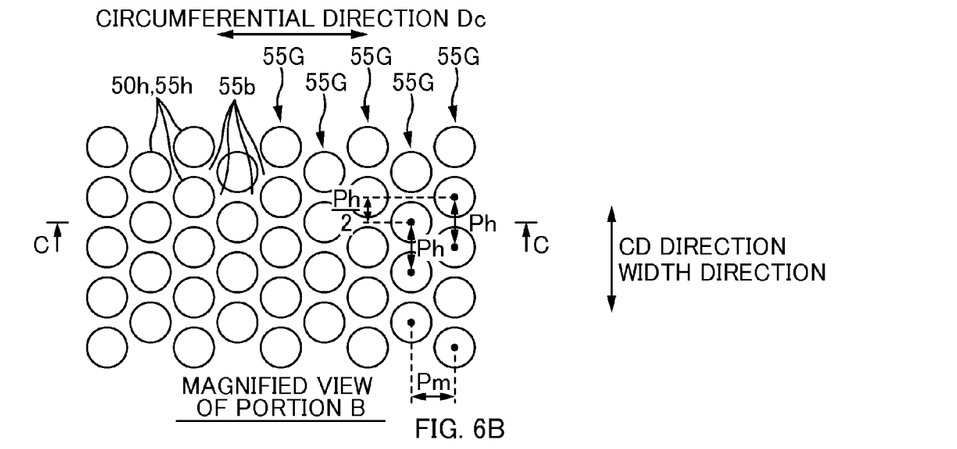
FIG. 6B is an enlarged diagram of a portion B in FIG. 6A.
Figure 6C:
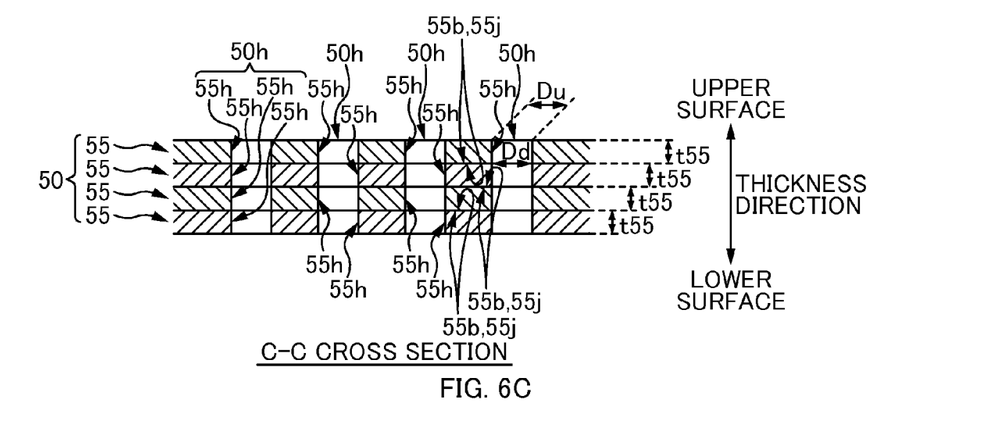
FIG. 6C is a cross-sectional view taken along line C-C in FIG. 6B.

FIGS. 6A to 6C show explanatory diagrams of the air-permeable member 50 according to the present embodiment. FIG. 6A is a plan view of the air-permeable member 50 in a state where it is attached to the shaping mold plate 27, FIG. 6B is an enlarged view of a portion B in FIG. 6A, and FIG. 6C is a cross-sectional view taken along line C-C in FIG. 6B.

As shown in FIG. 6A, the air-permeable member 50 is a plate-like member having an approximately rectangular shape when viewed from above. The air-permeable member 50 has the plurality of air holes 50h penetrating this plate-like member in the thickness direction. Due to these air holes 50h, the air-permeable member 50 allows the passage of air in the thickness direction, but restricts the passage of the pulp fibers 2 in the thickness direction.

The main body of the air-permeable member 50 is a plate-layered body 50 in which a plurality of (four, in the example shown in FIG. 6C) plates 55 each having a predetermined thickness are stacked in the thickness direction and integrally joined together. The number of the plates that are stacked is, for example, four to twenty depending on conditions such as the thickness and the material of each plate 55. Thus, the thickness of the air-permeable member 50 is set at, for example, 0.4 mm to 2.0 mm.

With regard to the material of each plate 55, a metal plate such as a steel plate or a non-ferrous metal plate is preferable. In this example, a stainless steel plate (SUS304) is used. However, a non-metal plate such as a resin plate can also be used as long as it has certain degrees of rigidity and strength.

As shown in FIG. 6A, the planar shape of each plate 55 is designed so as to be a shape that corresponds to the opening portion 27a of the shaping mold plate 27 and covers the opening portion 27a, and is approximately rectangular in this example. Moreover, although all the plates 55 are made so as to have the same planar shape in this example, It is not necessary that all the plates 55 have the same planar shape.

The thickness t55 of each plate 55 is selected from a range of, for example, 0.05 mm to 0.5 mm, and the thickness t55 is substantially uniform throughout the plate 55. It should be noted that in this example, the thickness t55 is 0.1 mm.

As shown in FIG. 6C, a plurality of air holes 55h, 55h, . . . are formed through each plate 55 in the thickness direction. Each air hole 55h is a perfect circular hole and the diameter thereof is set at 0.2 to 0.25 mm, for example. Moreover, in all of the plates 55 constituting the above-described plate-layered body 50, these air holes 55h, 55h . . . are arranged in the same arrangement pattern (a staggered pattern in the example shown in FIGS. 6A and 6B).

Accordingly, as shown in FIG. 6C, each air hole 55h of the plates 55 corresponds to the air hole 55h of an plate 55 adjacent in the thickness direction, and the air hole 55h substantially concentrically communicates with the corresponding air hole 55h. Moreover, the corresponding air holes 55h, 55h . . . of all plates 55 stacked in the thickness direction have the same planar shape. For example, if one air hole 55*h* of corresponding air holes 55*h*, 55*h* . . . is a perfect circular hole having a diameter of 0.2 mm, all of the other air holes 55*h*, 55*h* . . . are perfect circular holes having a diameter of 0.2 mm. Furthermore, the thickness t55 of each plate 55 takes any value within the above-described range of 0.05 mm to 0.5 mm and is sufficiently thin. Therefore, even when an etching method is used to form these holes, the resulting holes 55*h* have only a slight difference between the hole diameter Du on the upper surface side and the hole diameter Dd on the lower surface side. That is, the air holes 55*h*, 55*h*, . . . of each plate 55 that are formed by this etching method are ones that have a substantially straight-sided shape whose cross-sectional shape when viewed from the thickness direction is maintained substantially uniform throughout the thickness direction.

Therefore, each air hole 50*h* of the air-permeable member 50, which is formed by the air holes 55*h*, 55*h*, . . . of the plates 55, 55, . . . communicating in the thickness direction, has a generally straight-sided shape as a whole (see FIG. 6C). This makes it possible to effectively prevent the air-permeable member 50 from clogging when the pulp fibers 2 are being deposited. Also, the straight-sided shape reduces a pressure loss of air passing therethrough, and also excels in terms of the energy efficiency during deposition.

Moreover, in this air-permeable member 50, a joining portion 55*j* that joins adjacent plates 55 and 55 in the thickness direction is formed in a portion 55*b* of each plate 55 in which the air holes 55*h*, 55*h*, . . . are not formed (hereinafter also referred to as "no-air-hole portion 55*b*"). That is to say, adjacent plates 55 and 55 in the thickness direction are joined to each other by the no-air-hole portion 55*b* in surface-to-surface contact (in close contact).

This enables a joining area of the joining portion 55*j* to be as large as possible and can increase the joining strength between the plates 55 and 55. Also, this can effectively increase the level of integration of a certain no-air-hole portion 55*b* with its adjacent no-air-hole portion 55*b* in the thickness direction, so that the strength of the no-air-hole portions 55*b* themselves is also improved. Consequently, it is possible to prevent effectively the fatigue failure starting from the no-air-hole portions 55*b*, and to increase the durability of the air-permeable member 50.

Furthermore, since the air-permeable member 50 is composed of the plurality of plates 55 that are stacked and integrally joined together, the air-permeable member 50 has enhanced rigidity and is not easily deformed. Accordingly, the bending deformation of each plate 55 that may repeatedly occur during the deposition of the pulp fibers 2 is also reduced as a whole, and therefore the bending stress that acts on the no-air-hole portions 55*b* is also reduced. This also effectively contributes to the prevention of the above-described fatigue failure of the no-air-hole portions 55*b*.

Examples of the arrangement pattern of the air holes 55*h*, 55*h* . . . include a grid pattern, a staggered pattern, and the like, and in this example shown in FIGS. 6A and 6B, a staggered pattern is adopted. Specifically, in this staggered pattern, air hole rows 55G are provided by lining up a plurality of air holes 55*h*, 55*h*, . . . at a predetermined pitch Ph (0.3 mm in this example) along the CD direction, which is the width direction of the rotating drum 20, and the basic pattern thereof is that the position of each air hole row 55G is shifted half a pitch (=Ph/2) in the CD direction with respect to the position of the adjacent air hole row 55G in the circumferential direction Dc. However, in this example, in addition to this condition, a pitch Pm at which the air hole rows 55G are arranged in the circumferential direction Dc is set to a pitch defined by a formula: Pm=Ph×cos 30°. This allows making equal the distances between each of adjacent air holes 55*h*. It can be said that a unit of the arrangement pattern of this example is a pattern that each vertex of an equilateral triangle is the position of each air hole 55*h*, and that the arrangement pattern is formed by repeating the unit across a substantially entire area. The length of each side of the equilateral triangle is equal to the above-described Ph, for example, 0.3 mm.

With the staggered pattern as described above, the air holes 55*h* (50*h*) are closely arranged at a high density. Accordingly, for example, the aperture ratio of the air-permeable member 50 can be set at a value as high as 50% to 63%, so that the deposition efficiency of the pulp fibers 2 on the air-permeable member 50 can be enhanced.

An example of the method that can form air holes 55*h* in the foregoing dense arrangement is an etching method. That is to say, in the etching method, regions corresponding to the no-air-hole portions 55*b* on a plate 55 are first masked with a corrosion inhibitor based on the above-described arrangement pattern. Then, only regions corresponding to the air holes 55*h* are selectively corroded by, for example, applying an etchant to substantially the entire surface of the plate 55 over the mask, the holes 55*h* is formed completely through the plate 55. Thus, the air holes 55*h* are formed in the above-described arrangement pattern.

When the thickness t55 is defined as A mm and the diameter of the air holes 55*h* is defined as B mm, it is desirable that A and B are set so as to satisfy the relationship of Formula 1 below when the thickness t55 of the plate 55 is within the range of 0.05 mm to 0.5 mm.

$$B = 1.2 \text{ A to } 1.66 \text{ A} \tag{1}$$

In this manner, this etching method can achieve holes 55*h* with high straightness while maintaining the strength of the plate 55.

Figure 7A:
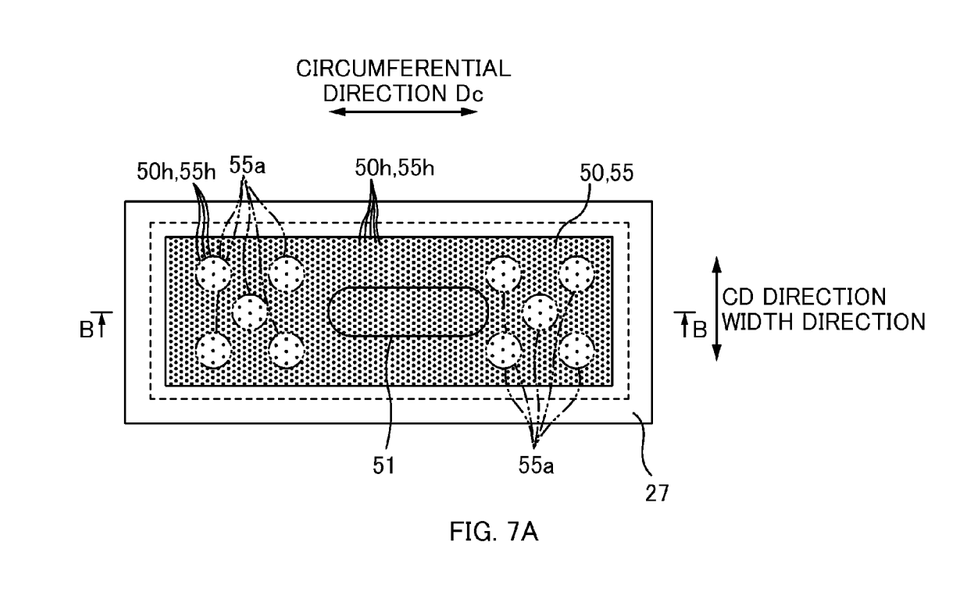
FIG. 7A is a plan view of a plate 55 having regions 55a in which the air holes 55h are arranged at a different density.

Moreover, it is not necessary to make the arrangement density of the air holes 55*h* uniform throughout the plate 55. Alternatively, a region may also be provided in which the arrangement density is different. For example, in the example shown in FIG. 7A, in order to provide in the absorbent body 1 local portions of small basis weight, the regions 55*a* of the plate 55 corresponding to those portions are low-density regions 55*a* in which the arrangement density of the air holes 55*h* is lower than that of surrounding regions.

An example of the method for joining plates 55 to each other is diffusion welding. Diffusion welding refers to "a method in which a joint can be achieved in intimate contact of the workpieces at a temperature below the melting point of the workpieces under such pressure that plastic deformation can be suppressed as much as possible, by using diffusion of atoms across the interface" (see the Japanese Industrial Standards JIS Z3001-2: 22702).

For example, in the case where SUS304 is used as the material for all of the plates 55, the joining process is performed in the following manner. First, prepare plates 55 the number of which is as many as to be stacked, the plates 55 having the air holes 55*h* formed by the above-described etching method. Subsequently, as shown in FIG. 6C, heat the stacked plates 55, 55, . . . at a temperature not more than the melting point of SUS304, for example within a range of 800 to 1200° C. At the same time, press the stacked plates 55 in a vertical direction while being sandwiched with a pressing member (not shown). Therefore, the stacked plates 55 are joined to each other at their no-air-hole portions 55*b* that are in contact with each other, and thus the above-described air-permeable member 50 is formed.

Diffusion welding as described above directly joins the base materials of adjacent plates 55 to each other at the no-air-hole portions 55*b*. Accordingly, it can be said that adjacent no-air-hole portions 55*b* in the thickness direction are joined to each other without an interposer. Therefore, the joining strength between those no-air-hole portions 55*b* can be enhanced.

As described below, if pressing is to be performed after diffusion welding, it is preferable that, in order to increase the workability (plastic deformation capacity) in processing, the foregoing diffusion welding is performed under inert gas atmosphere such as argon gas, nitrogen gas.

The air holes 55*h* are minute holes as described above. Therefore, when stacking the plates 55, 55 . . . in order to form the plate-layered body 50, the planar positions of corresponding air holes 55*h* are less likely to be aligned between plates 55. As a result, there is a possibility that the adjacent air holes 55*h* in the thickness direction which should correspond to and be in communication with each other are not in communication with each other.

Figure 8:
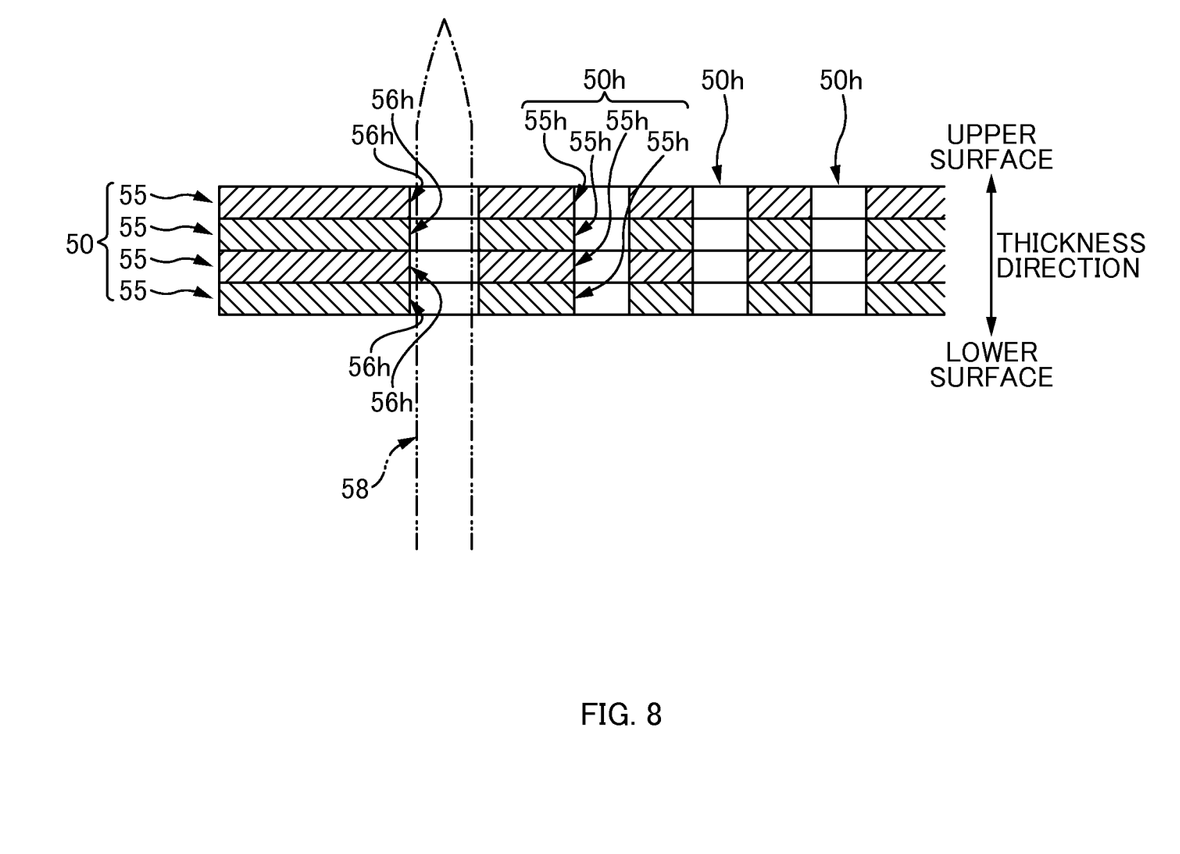
FIG. 8 is a cross-sectional view of plates 55 that are provided with a reference hole 56h.

Thus, it is desirable that a reference hole 56*h* for positioning, which is different from the air holes 55*h*, are formed in each plate 55, as shown in the cross-sectional view of FIG. 8. This reference hole 56*h* is formed in each of the plates 55 such that the planar positional relationship of the reference hole 56*h* with the air holes 55*h* on the plate 55 is the same for all of the plates 55. More specifically, the reference hole 56*h* is formed such that adjacent reference holes 56*h* in the thickness direction substantially concentrically communicate with each other when corresponding air holes 55*h* of all plates 55 stacked in the thickness direction substantially concentrically communicate with each other.

Accordingly, suppose a bar member 58 is inserted into the reference holes 56*h* so as to penetrate the stacked plates 55 in the thickness direction or so as to penetrate the plates 55 while stacking these plates 55 in the thickness direction. In this case, the positions of corresponding air holes 55*h* of these plates 55 are adjusted so that the corresponding air holes 55*h* substantially concentrically communicate with each other. Then, the foregoing diffusion welding with the bar member 58 being inserted prevents the misalignment of the air holes 55*h* between plates 55.

As shown in FIG. 6A, it is desirable that a position in each plate 55 at which the reference hole 56*h* is formed is set in a portion that is closer to the outer circumferential edge of the plate 55 than the formation area of the air holes 55*h* is and that comes into contact with the shaping mold plate 27 when being attached to shaping mold plate 27. With this setting, when the air-permeable member 50 has been attached to the rotating drum 20, the reference holes 56*h* are covered by the circumferential edge portion of the opening portion 27*a* of the shaping mold plate 27 and do not allow the passage of air. Thus the reference holes 56*h* does not affect the deposition of the absorbent body 1.

Moreover, two or more reference holes 56*h* are provided for each plate 55. This is because defining the positions of two points enables the relative positional relationship between plates 55 to be fixed. In the example shown in FIG. 6A, the reference holes 56*h* are respectively formed in a pair of corner portions, of the four corner portions of the plate 55, that are diagonally opposite to each other. These reference holes 56*h* are also formed at the same time with the air holes 55*h* by, for example, the above-described etching method.

Figure 5:
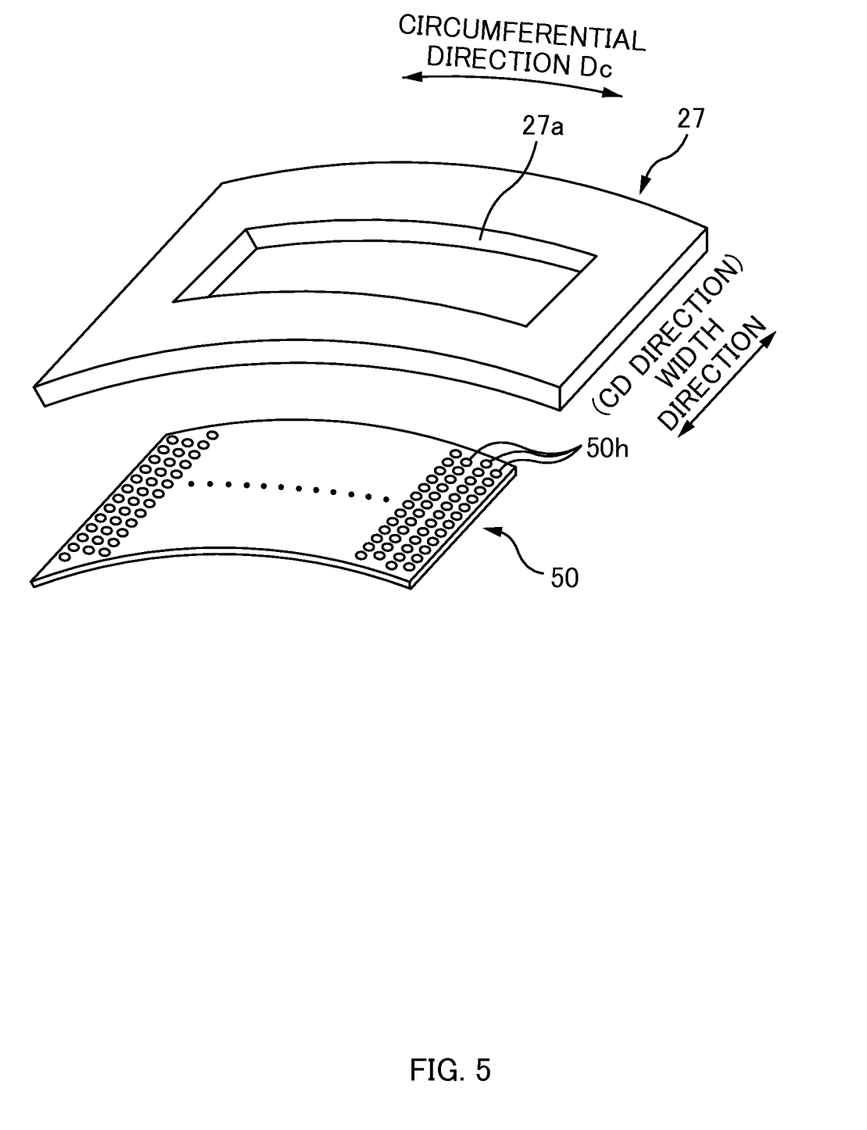
FIG. 5 is an exploded perspective view of a shaping mold plate 27.

Since the shaping mold plates 27 to which these air-permeable members 50 are to be attached have an arcuate shape as shown in FIG. 5, the air-permeable members 50 are required to be curved so as to conform to the curvature of an inner circumferential surface of the shaping mold plates 27. Moreover, if the absorbent body 1 is required to be shaped into a three-dimensional shape having a local region with a different basis weight, it is necessary to form in the air-permeable members 50 a depression or a protrusion corresponding to that three-dimensional shape.

Figure 7B:
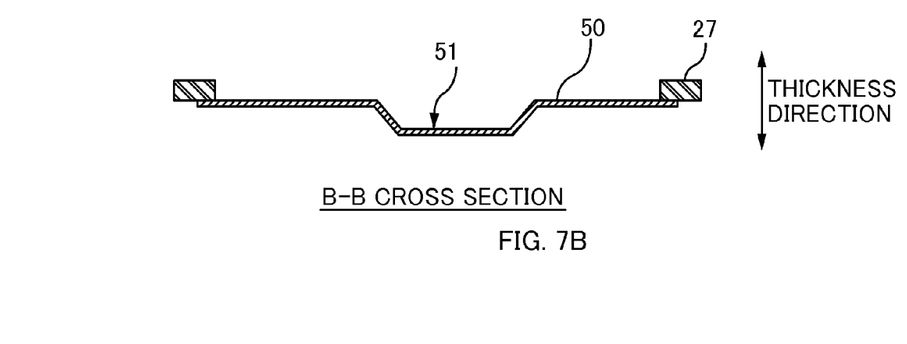
FIG. 7B is a cross-sectional view taken along line B-B in FIG. 7A.

The curving and forming of a depression or a protrusion are performed, after integrating the air-permeable member 50 by diffusion welding, by pressing the air-permeable member 50 while keeping its integrated state. FIG. 7B shows a cross-sectional view taken along line B-B in FIG. 7A, and in this example, the target three-dimensional shape of the air-permeable member 50 has a depression 51 that is depressed in the thickness direction. Therefore, as press mold, used are a male press mold and a female press mold that have a curved shape as a whole and that provide a depression or a protrusion corresponding to the depression 51. In addition, by sandwiching and pressing the plate-layered body 50 between these male and female press molds, the plate-layered body 50 undergoes plastic deformation, and the curved shape and the depression 51 are formed thereon.

It should be noted that it is evident that the method for manufacturing the air-permeable member 50 can be achieved by combining the following processes: the process of forming the air holes 55*h* in each plate 55 by the above-described etching method; the process of stacking the plates 55 in the thickness direction, which has been explained in the foregoing description regarding diffusion welding; and the process of joining the stacked plates 55 by the above-described diffusion welding. Therefore, a detailed description of the manufacturing method will be omitted.

Other Embodiments

In the foregoing, an embodiment of the invention was described. However, the invention is not limited to this embodiment, and modifications as described below are possible.

In the foregoing embodiment, perfect circular holes are described as an example of the air holes 55*h* of the plates 55. However, the shape of the air holes 55*h* is not limited to a perfect circular shape when viewed from above. For example, the air holes 55*h* may also have an elliptical shape when viewed from above, or may also have a polygonal shape, such as a triangular shape or a rectangular shape, when viewed from above. Incidentally, if the planar shape of the air holes 55*h* is set to a perfect hexagonal shape, the air holes 55*h* can be densely arranged on the plates 55.

Moreover, in the foregoing embodiment, the plurality of air holes 55*h* that are formed in and throughout the plate 55 have the same planar shape (e.g., a perfect circular shape). However, the invention is not limited to this. The planar shape of the air holes 55*h* may be different depending on the planar position. Even in this case, however, it goes without saying that adjacent air holes 55*h* in the thickness direction which should communicate with each other are formed into the same shape. This is because the air-permeable member 50 is the plate-layered body formed from the stacked plates 55 and the air holes 50*h* thereof have substantially straight-sided shape as a whole.

Figure 9A:
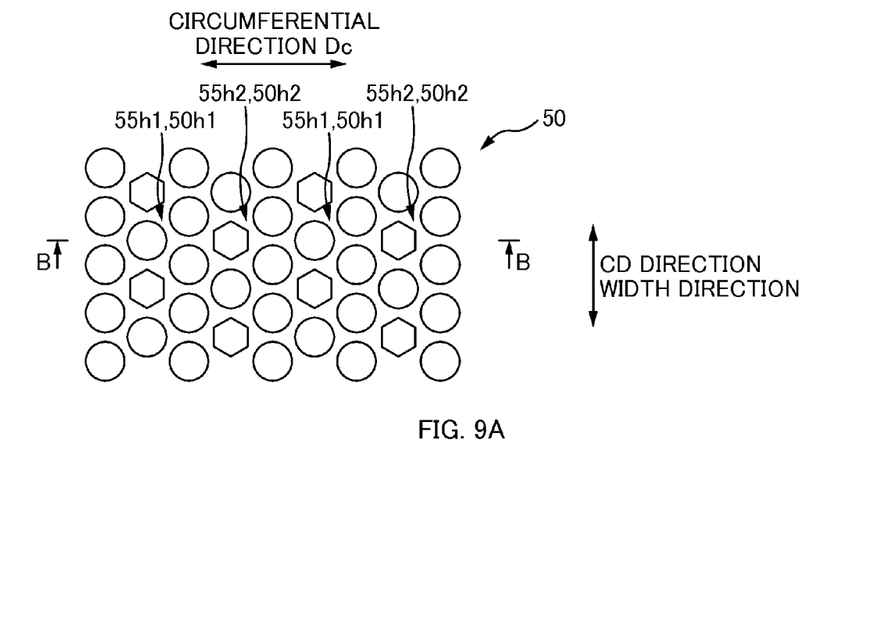
FIG. 9A is a plan view of an air-permeable member 50 according to other embodiments.
Figure 9B:
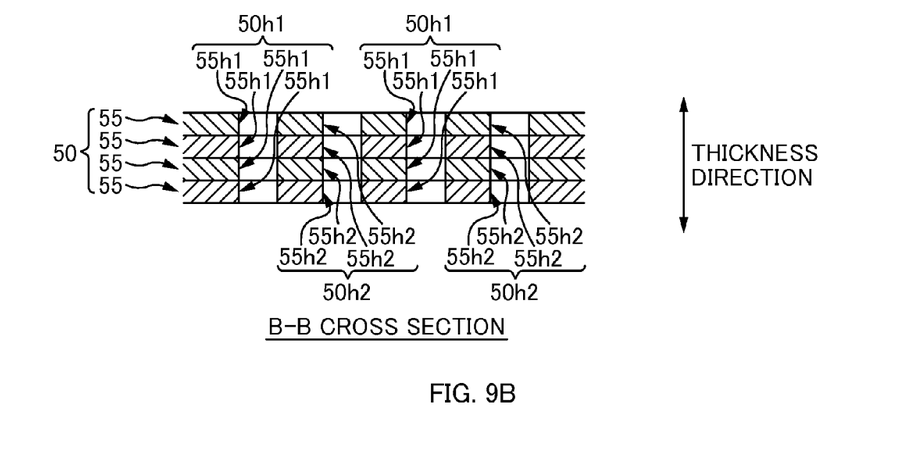
FIG. 9B is a cross-sectional view taken along line B-B in FIG. 9A.

An example thereof is shown in FIGS. 9A and 9B. FIG. 9A is a plan view, and FIG. 9B is a cross-sectional view taken along line B-B in FIG. 9A. In this plate 55, two types of air holes 55*h*1 and 55*h*2 are formed which have mutually different planar shapes. Specifically, the first air holes 55h1 have a circular shape, while the second air holes 55h2 have a hexagonal shape.

However, all of the first air holes 55h1, 55h1 . . . which are adjacent in the thickness direction have the same circular planar shape, and all of the second air holes 55h2, 55h2 . . . which are adjacent in the thickness direction have the same hexagonal planar shape. Thus, each air hole 50h1 of the air-permeable member 50 in which the first air holes 55h1, 55h1 . . . communicate with each other has a substantially straight-sided shape, and each air hole 50h2 of the air-permeable member 50 in which the second air holes 55h2, 55h2 . . . communicate with each other has a substantially straight-sided shape.

Suppose the planar shape of the air holes 55h is not such a perfect circular shape as that of the first air holes 55h1, but rather is a shape whose distance from the center to the circumferential surface of the holes varies in the circumferential direction as the second air holes 55h2. In other words, suppose the planar shape of the air holes 55h varies depending on the orientation. In this case, it is desirable that the orientations of the planar shapes of all the adjacent air holes 55h in the thickness direction are set to the same single direction. In this manner, the air holes 50h2 of the resulting air-permeable member 50 can have a more straight-sided shape. For example, in the case where the air holes 55h have such a perfect hexagonal shape as the second air holes 55h2 in FIG. 9A, it is preferable that the orientations of the corners of all the adjacent air holes 55h2 in the thickness direction are set to the same single direction. In the case where the air holes 55h have an elliptical shape, it is preferable that the orientations of the major axes of all the adjacent air holes 55h2 in the thickness direction are set to the same single direction.

In the foregoing embodiment, all of the plurality of plates 55 constituting the air-permeable member 50 had the same thickness. However, the invention is not limited to this, and the plates 55 may also have different thicknesses.

LIST OF REFERENCE NUMERALS

1 absorbent body, 2 pulp fiber (liquid absorbent material),
3 mixed air (air),
10 fiber depositing apparatus (apparatus for manufacturing absorbent body),
20 rotating drum, 20a outer circumferential surface, 21 shaping mold,
22a cylindrical partition wall, 22b partition wall,
23 ring member, 23a circumferential edge, 24 circular wall,
25 coupling plate,
27 shaping mold plate, 27a opening portion,
31 supply duct, 31a supply opening portion,
41 suction conveyor,
50 air-permeable member, 50h air hole, 50h1 air hole, 50h2 air hole,
51 depression,
55 plate, 55h air hole, 55G air hole row,
55h1 air hole, 55h2 air hole,
55a low-density region, 55b no-air-hole portion,
55j joining portion,
56h reference hole, 58 bar member,
Z1 first zone, Z2 second zone, C20 horizontal axis, S substantially closed space

The invention claimed is:

1. A method for manufacturing an air-permeable member, the air-permeable member being used when shaping an absorbent body of an absorbent article by depositing a liquid absorbent material,
the air-permeable member allowing an air that contains the liquid absorbent material to pass in a thickness direction of the air-permeable member,
the air-permeable member restricting passage of the liquid absorbent material,
the method comprising:
forming a plurality of plates each of which has a plurality of air holes that penetrate the plate in the thickness direction,
the forming including forming air holes of the plurality of air holes into a same shape, the air holes being ones that exist in all of the plates to be stacked and that should communicate with one another;
stacking the plurality of plates in the thickness direction while adjusting adjacent air holes in the thickness direction so that the adjacent air holes communicate with one another; and
joining adjacent plates of all of the stacked plates at a portion in which the air holes are not formed
wherein
the air-permeable member is configured to cover an opening portion which has a shape corresponding to a shape into which the absorbent body is to be formed, the opening portion being formed in a shaping mold plate,
each of the air holes of each plates communicates with one of the air holes provided at a neighboring plate in the thickness direction,
each of the plates has at least two reference holes that are different from the air holes and that penetrate the plate in the thickness direction,
the reference holes are formed so that adjacent reference holes in the thickness direction communicate with one another when corresponding air holes of all of the plates stacked in the thickness direction communicate with one another, the reference holes are formed in a portion that is closer to an outer circumferential edge of the each of the plates than a formation area of the air holes is and that comes into contact with the shaping mold plate when being attached to shaping mold plate.

2. A method for manufacturing an air-permeable member according to claim 1, wherein
the method further comprises forming in each of the plurality of plates at least two reference holes that are different from the air holes and that penetrate the plate in the thickness direction, In the forming of the reference holes,
the reference holes are formed so that adjacent reference holes in the thickness direction communicate with one another when corresponding air holes of all of the plates stacked in the thickness direction communicate with one another.

3. A method for manufacturing an air-permeable member according to claim 2, wherein
in the stacking, a bar member is inserted into adjacent reference holes in the thickness direction
so as to penetrate the plurality of plates that have been stacked or
so as to penetrate the plurality of plates while stacking the plurality of plates.

4. A method for manufacturing an air-permeable member according to claim 3, wherein in the joining step, In a state where the bar member has been inserted into the reference holes, the adjacent plates are joined by diffusion welding at the portion in which the air holes are not formed.

\* \* \* \* \*